US007103416B2

(12) United States Patent
Ok et al.

(10) Patent No.: US 7,103,416 B2
(45) Date of Patent: Sep. 5, 2006

(54) VISUAL PROSTHESIS INCLUDING ENHANCED RECEIVING AND STIMULATING PORTION

(75) Inventors: Jerry Ok, Glendale, CA (US); Robert J. Greenberg, Los Angeles, CA (US); Mark Humayun, Timonium, MD (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 09/761,270

(22) Filed: Jan. 16, 2001

(65) Prior Publication Data

US 2002/0095193 A1 Jul. 18, 2002

(51) Int. Cl.
*A61N 1/08* (2006.01)

(52) U.S. Cl. .............................. 607/54; 607/53; 607/61; 607/116; 623/4.1; 623/6.63

(58) Field of Classification Search .................. 607/54, 607/53, 61, 116, 50, 60, 65, 141; 623/4.1, 623/11.11, 24, 6.63

See application file for complete search history.

(56) References Cited

U.S. PATENT DOCUMENTS 4,628,933 A * 12/1986 Michelson .................. 607/53
5,556,423 A * 9/1996 Chow et al. .................. 607/54
5,935,155 A 8/1999 Humayun et al.
5,944,747 A * 8/1999 Greenberg et al. ............ 607/54
6,298,270 B1 * 10/2001 Nisch et al. .................. 607/54
6,347,250 B1 * 2/2002 Nisch et al. .................. 607/54
6,389,317 B1 * 5/2002 Chow et al. .................. 607/54
6,393,327 B1 * 5/2002 Scribner ...................... 607/54
6,427,087 B1 * 7/2002 Chow et al. .................. 607/54
6,507,758 B1 * 1/2003 Greenberg et al. ............ 607/54

OTHER PUBLICATIONS

M. Schwarz, et al., Hardware Architecture of a Neural Net Based Retina Implant for Patients suffering from Retinitis Pigmentosa, 1996 IEEE International Conference on Neural Networks.

* cited by examiner

*Primary Examiner*—Sang Y. Paik
*Assistant Examiner*—Fadi H. Dahbour
(74) *Attorney, Agent, or Firm*—Thomas Lendval; Scott B. Dunbar

(57) ABSTRACT

A visual prosthesis including an enhanced receiving and stimulating portion for electrically stimulating retinal tissue to present an apparent image to a user. The prosthesis includes an extracellular camera which responds to a real image to generate a real image signal. The real image signal is coupled, e.g., RF coupling, from an extracellular primary coil to a secondary coil. The secondary coil is preferably affixed within the vitreous body of the user's eye positioned for good signal coupling to the primary coil and arranged to be in good thermal contact with the vitreous body which acts as a heat sink. A hermetically sealed housing containing signal processing circuitry is also preferably placed in the vitreous body to assure efficient heat transfer away from the housing. The circuitry is electrically connected to the secondary coil and responds to an output signal therefrom to produce an apparent image signal for driving an electrode array. The electrode array is configured to electrically stimulate the eye's retinal tissue to enable a user to perceive an apparent image.

21 Claims, 5 Drawing Sheets

VISUAL PROSTHESIS INCLUDING ENHANCED RECEIVING AND STIMULATING PORTION

FIELD OF THE INVENTION

This invention relates generally to a visual prosthesis for restoring at least partial vision to a user afflicted with photoceptor degeneration.

BACKGROUND OF THE INVENTION

U.S. Pat. No. 5,935,155 describes a visual prosthesis generally comprised of (1) an image acquiring and transmitting portion and (2) a receiving and retina stimulating portion. The acquiring portion includes a camera for generating a visual signal output representative of an acquired image. The stimulating portion includes an electrode array adapted to be operatively attached to the user's retina. The visual signal output is used to modulate a radio frequency (RF) carrier signal which is applied to a primary coil. A secondary coil receives the RF signal which is then demodulated to recover the visual signal output for driving the electrode array to electrically stimulate retinal tissue. In use, the acquiring and transmitting portion is mounted outside of the eye (extracellular) and the receiving and stimulating portion is primarily mounted in the eye (intraocular) The components of the intraocular portion are powered from energy extracted from the transmitted visual signal.

FIG. 1 of U.S. Pat. No. 5,935,155 comprises a functional block diagram of the visual prosthesis showing its image acquiring and transmitting portion and its receiving and retina stimulating portion. FIGS. 2 and 3 respectively show the organization of functional components of the respective portions of FIG. 1. FIGS. 4, 5, and 6 depict alternative arrangements for deploying the prosthesis physical components. In all of the figures, the primary coil is mounted in alignment with the optic axis in front of the eye, e.g., in an eyeglass lens, frame, or in a soft contact lens. In FIG. 4, the secondary coil is implanted behind the iris and a circuit housing is collocated therewith. In FIG. 5, the secondary coil is implanted behind the iris but the circuit housing is located outside of the sclera wall. In FIG. 6, the secondary coil is placed adjacent the outer sclera surface. U.S. Pat. Nos. 5,800,530 and 6,120,538 describe alternative visual prostheses.

SUMMARY OF THE INVENTION

The present invention is directed to a visual prosthesis and more particularly to an enhanced receiving and stimulating portion for electrically stimulating retinal tissue to present an apparent image to a user. Visual prosthesis embodiments in accordance with the invention utilize an image acquiring and transmitting portion having an extracellular camera and primary coil. The camera responds to a real image to generate a real image signal which is coupled, e.g., RF coupling, from the primary coil to the secondary coil of the receiving and stimulating portion.

In accordance with a first preferred embodiment of the invention, the secondary coil is placed within the vitreous body of the user's eye positioned and oriented for good signal coupling to the extracellular primary coil. For example, both coils are located in close proximity substantially coincident with the optic axis of the user's eye. Moreover, the secondary coil is arranged to be in good thermal contact with the vitreous body which acts as a heat sink.

In accordance with a significant aspect of the first preferred embodiment, a signal processing circuitry electrically connected to the secondary coil is also placed in the vitreous body to assure efficient heat transfer therefrom. The circuitry is preferably contained in a protective hermetically sealed housing which preferably comprises a metal can but which also can constitute any coating or envelope for protecting the circuitry from adverse effects of salt water. The circuitry responds to an output signal from the secondary coil to produce an apparent image signal for driving an electrode array. The electrode array is configured to electrically stimulate the eye's retinal tissue to enable a user to perceive an apparent image.

In accordance with a further feature of the preferred embodiment, the housing, which is preferably metal, is placed and/or oriented in a manner to minimize the generation of eddy currents in the housing wall which would diminish energy transmission efficiency, In one arrangement, the housing is located posteriorly of the secondary coil but oriented with its shortest dimensions perpendicular to the secondary coil axis. In an alternative arrangement, the housing is displaced from the secondary coil axis but in substantially the same plane as the secondary coil.

In a still further embodiment the invention, the housing is placed outside the sclera wall and electrically connected through the sclera to the secondary coil and retina electrode array.

In accordance with a still further prosthesis embodiment, the primary coil and secondary coil are both located to the side of the optic axis outside of the sclera wall enabling them to be closely coupled. The circuit housing is preferably located very close to the secondary coil and is electrically connected through the sclera to the retina electrode array.

DETAILED DESCRIPTION

Figure 1:
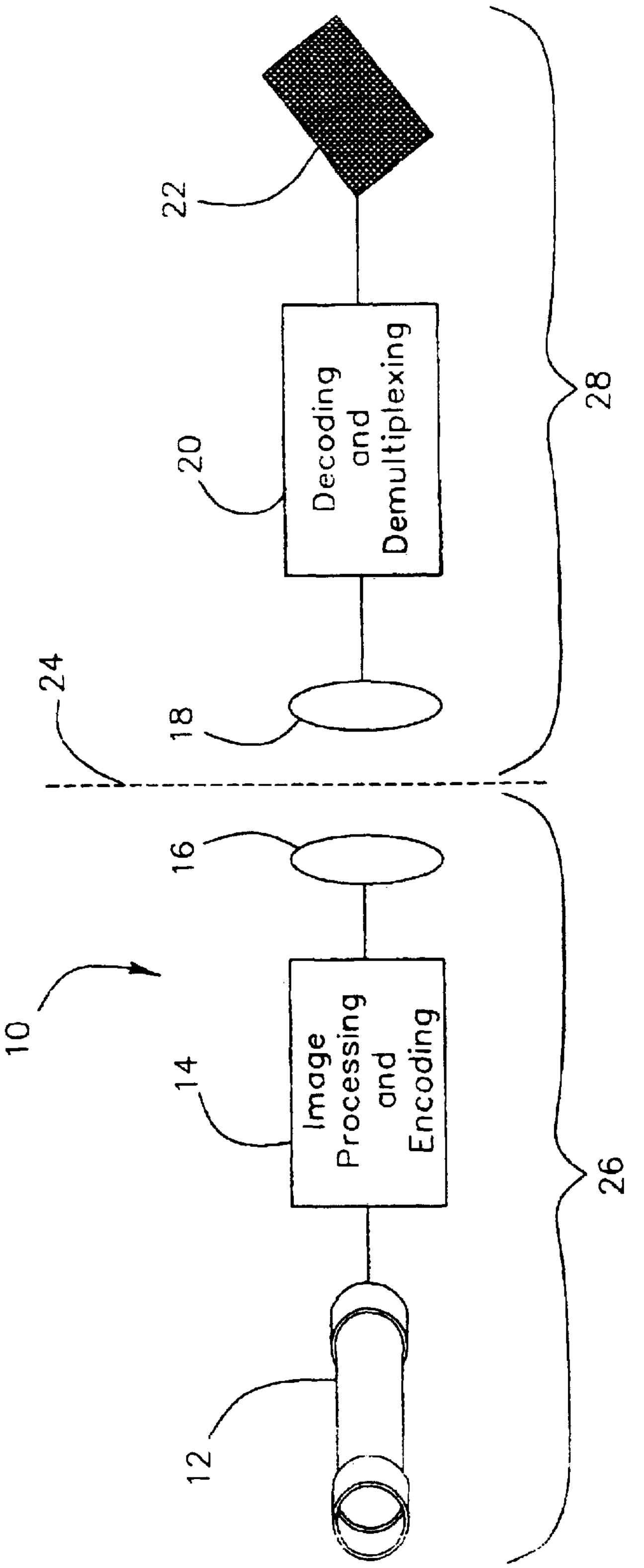
FIG. 1 is a functional block diagram of the visual prosthesis described in U.S. Pat. No. 5,935,155 showing its (1) image acquiring and transmitting portion and its (2) receiving and retina stimulating portion.

FIG. 1 depicts the visual prosthesis 10 of U.S. Pat. No. 5,935,155 which includes an image capturing element, such as a standard charge coupled device (CCD) camera 12, whose output is processed and encoded in circuit block 14. This processed and encoded captured real image signal is then coupled via primary coil 16 to a secondary coil 18. For example, the real image signal can be transmitted as a modulated radio frequency (RF) carrier signal. The secondary coil 18 receives the real image signal and applies an output signal to the signal processing circuit block 20. This circuit block 20 decodes and demultiplexes the applied signal and then communicates an apparent image signal to an electrode array 22 which stimulates the retinal cells to produce phoshenes in a pattern to simulate vision.

It should be noted that the dashed line 24 in FIG. 1 is included to functionally separate the image acquiring and transmitting portion 26 from the image receiving and stimulating portion 28 of the visual prosthesis 10. The dashed line 24 may or may not indicate the physical separation of extracellular and intraocular components as will be described more fully hereinafter with reference to FIGS. 4–7.

Figure 2:
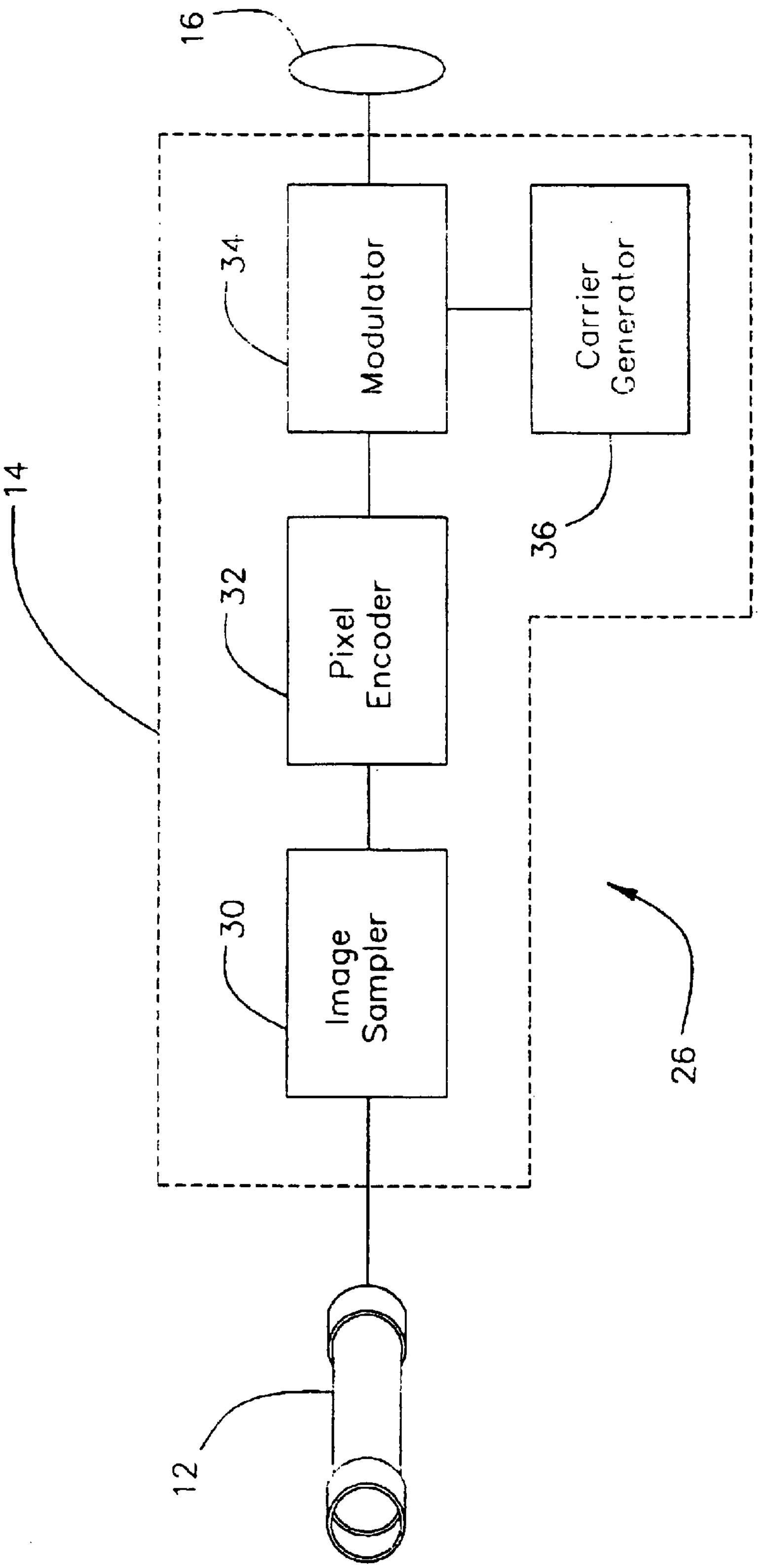
FIGS. 2 and 3 are functional block diagrams respectively showing the organization of the (1) image acquiring and transmitting portion and the (2) receiving and retina stimulating portion.

The image acquiring and transmitting portion 26 of the visual prosthesis 10 is illustrated in greater detail in FIG. 2 which shows the output of camera 12 coupled to an image sampler circuit 30 whose output is passed to a pixel encoder 32. The output of encoder 32 is passed to a signal modulator 34 which modulates a radio frequency carrier signal generated by the carrier generator 36. This RF signal is then applied to the primary coil 16.

The encoding scheme is preferably optimized for the target image resolution which is primarily determined by the size of the implanted electrode array. The encoded information typically includes such parameters as the magnitude, timing, and sequence of the stimulation pulses which will be generated by the electrode array to simulate the image through retinal stimulation.

Figure 3:
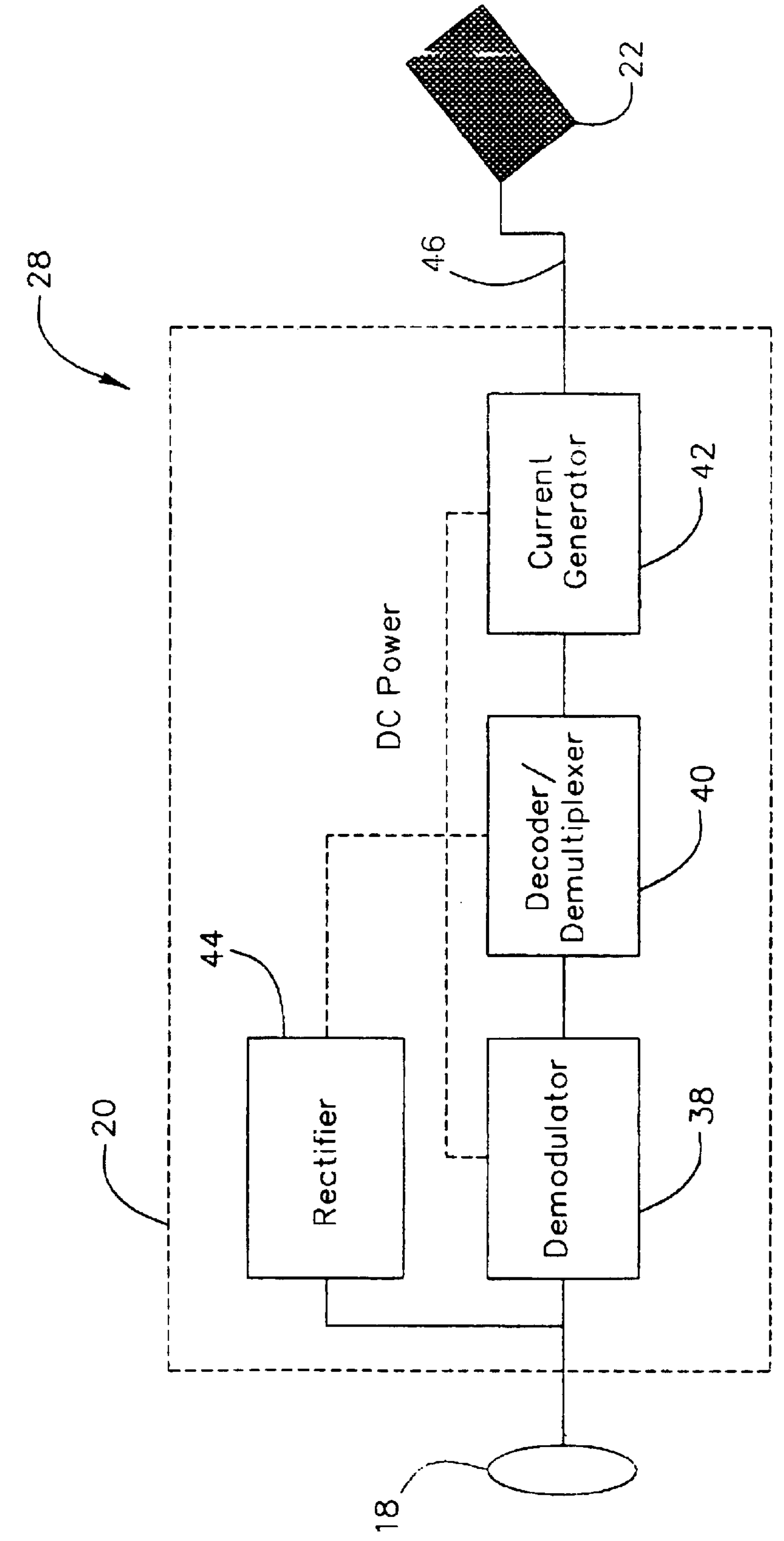

The RF signal applied to primary coil 16 is received by the secondary coil 18 of the stimulating portion 28 as illustrated in greater detail in FIG. 3. The secondary coil 18 output is passed to the demodulator 38 where the RF carrier signal is removed and the encoded image signal recovered. The encoded image signal is then passed to a decoder/demultiplexer 40 which in turn outputs the image information to a current generator 42 which drives the individual electrodes of the electrode array 22. The electric power for components of the image receiving and stimulating portion 28 is derived from the energy contained in the coupled RF signal through rectifier 44.

Figure 4:
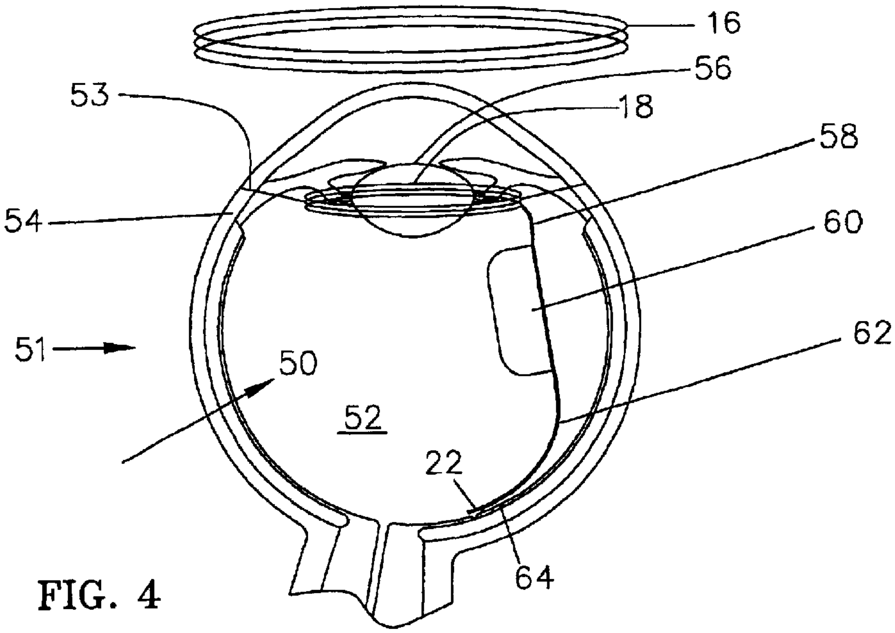
FIG. 4 depicts a simplified cross-section of an eye showing the placement of receiving and stimulating components in accordance with a first embodiment of the present invention.

Attention is now directed to FIG. 4 which depicts a first embodiment of the invention in which all of the components of the receiving and retina stimulating portion 28 are implanted in the vitreous chamber 50 of a user's eye 51. The chamber 50 is filled with the vitreous body 52 which comprises a clear colorless transparent jelly. As depicted in FIG. 4, the secondary coil 18 is fixed, e.g., by suture 53 to the adjacent sclera wall 54, just behind the lens 56. The secondary coil 18 is preferably axially aligned with the extracellular primary coil 16 and the optic axis of the eye. The respective coils are preferably mounted so that their planes are oriented substantially parallel to one another to achieve good signal coupling. The secondary coil 18 is physically and electrically connected 58 to signal processing circuitry 20 mounted in housing 60 which preferably comprises a metal can but which can constitute any coating or envelope capable of providing protection from the deleterious effects of salt water. The circuitry 20 in housing 60 is connected via conductor 62 to a flexible electrode array 22 physically and electrically contacting the user's retina 64.

It is significant to note that the secondary coil 18, housing 60 and electrode array 22 are all mounted in the vitreous body 52 in good thermal contact therewith. Thus, the vitreous body acts as a heat sink to cool the coil and electronic circuitry enabling the system to more efficiently utilize the signal energy derived from primary coil 16.

The housing 60 preferably comprises a hermetically sealed metal container having perpendicular width, depth, and length dimensions. In order to minimize eddy current induction into the housing wall, it is preferable to orient the housing with its smallest dimensions oriented parallel to the plane of coil 18 and preferably displaced from the coil axis.

Figure 5:
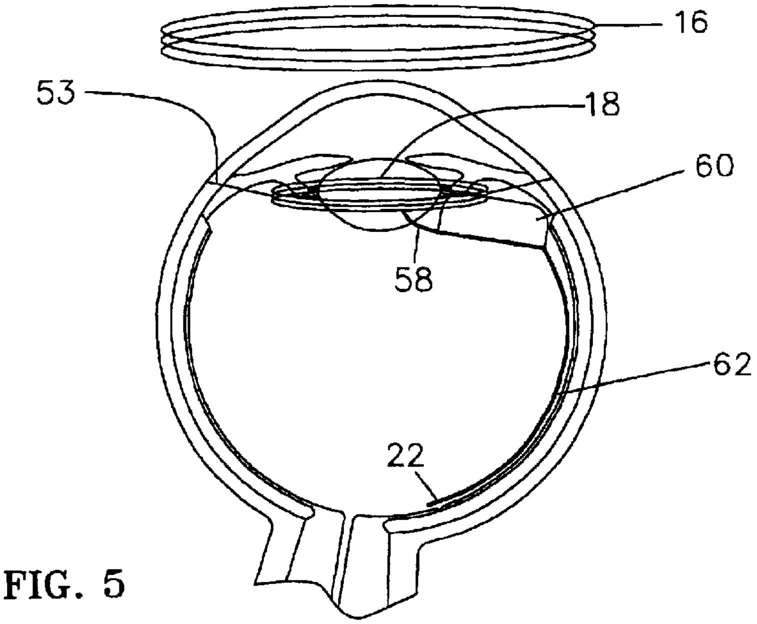
FIG. 5 depicts a simplified cross-section of an eye showing the placement of receiving and stimulating components in accordance with a second embodiment of the present invention.

Attention is now directed to FIG. 5 which differs from FIG. 4 in that housing 60 is placed to the side of coil 18 where it is fixed to the adjacent sclera wall, rather than hanging in the vitreous body as shown in FIG. 4. The arrangement of FIG. 5 offers greater mechanical stability and robustness than is available in FIG. 4.

Figure 6:
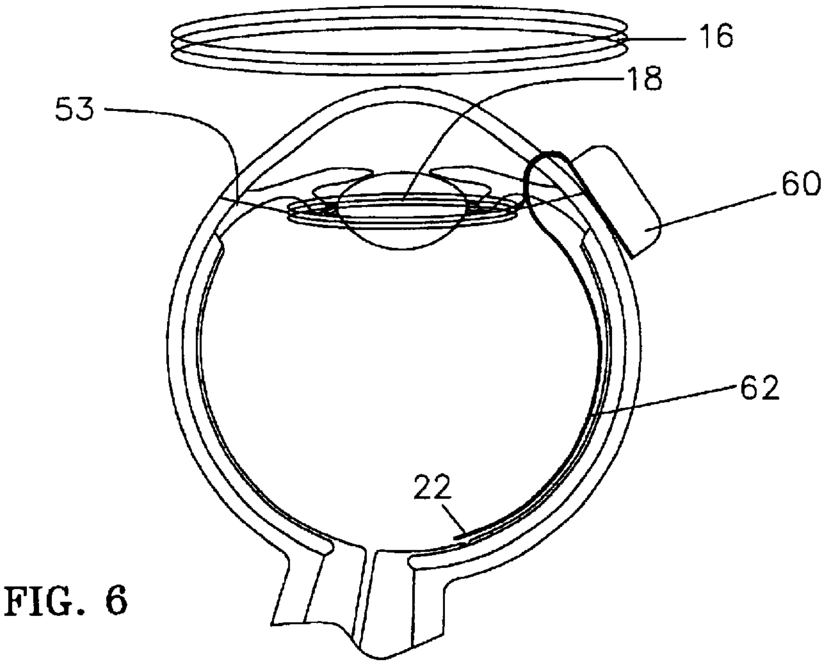
FIG. 6 depicts a simplified cross-section of an eye showing the placement of receiving and stimulating components in accordance with a third embodiment of the present invention.

FIG. 6 depicts a further embodiment in which the housing 60 is affixed to the extracellular side of the adjacent sclera wall. This housing placement has the advantage that essentially no eddy currents will be induced in the housing wall. Although housing placement is somewhat simplified relative to FIGS. 4 and 5, it nevertheless requires that conductive leads from the secondary coil and to the electrode array be passed through the sclera wall.

Figure 7:
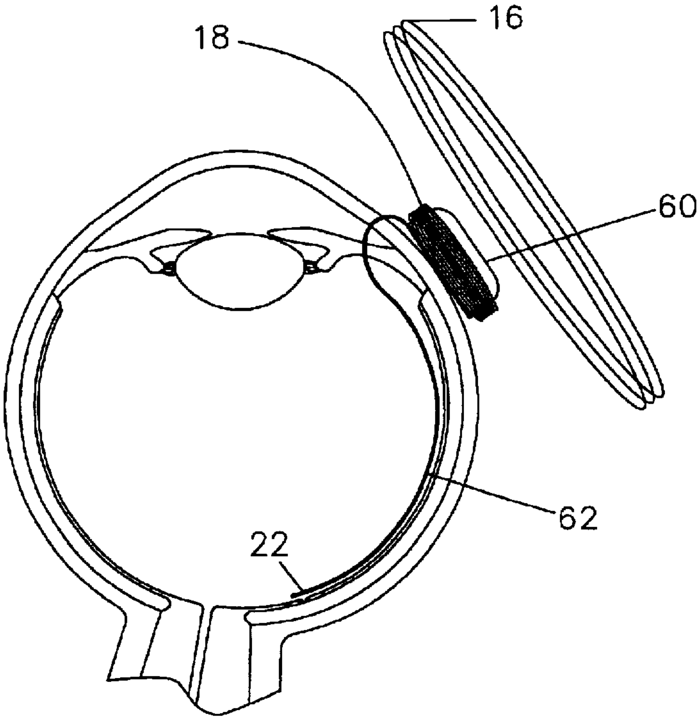
FIG. 7 depicts a simplified cross-section of an eye showing the placement of receiving and stimulating components in accordance with a fourth embodiment of the present invention.

FIG. 7 depicts a further alternative embodiment in which the housing 60 is mounted off-axis adjacent to the extracellular side of the adjacent sclera wall with the secondary coil 18 being wound around the housing. This collocation of housing and secondary coil offers the potential for miniaturization. Moreover, the off-axis placement of the secondary coil 18 enables the primary coil 16 to be mounted off-axis and in alignment as shown in FIG. 7. This off-axis placement may permit the coils 16, 18 to be placed closer together to increase signal coupling therebetween and the efficiency of the wireless transmission. As in FIG. 6, the arrangement of FIG. 7 requires that conductive leads pass through the sclera wall for connection to the electrode array 22.

From the foregoing, it should now be appreciated that several enhanced prosthesis embodiments have been described characterized by one or more of the following features:

1-secondary coil mounted within the vitreous body;

2-circuitry housing mounted within the vitreous body;

3-secondary coil and circuitry housing collocated outside of the sclera wall displaced from the optic axis.

Although only a limited number of embodiments have been specifically described, it is recognized that various modifications and alternatives will occur to those skilled in the art which fall within the spirit and scope of the invention as defined by the appended claims.

What is claimed is:

1. A prosthesis for at least partially restoring vision to a user suffering from a photoreceptor degenerative condition, said prosthesis including:

a secondary coil configured for mounting in the vitreous body of a user's eye for responding to a coupled input signal to produce an output signal;

an electrode array separate from said secondary coil, but electrically coupled to said secondary coil, and configured for implantation in said user's eye; and signal processing circuitry responsive to said output signal for applying an image signal to said electrode array for stimulating retinal cells in said user's eye.

2. The prosthesis of claim 1 wherein said signal processing circuitry is contained in a hermetically sealed housing configured for mounting in said vitreous body.

3. The prosthesis of claim 2 wherein said housing is oriented relative to said secondary coil to minimize the generation of eddy currents in said housing.

4. The prosthesis of claim 1 wherein said signal processing circuitry is contained in a protective housing configured for extracellular mounting; and further including conductive wires for electrically connecting said signal processing circuitry through the user's scleral wall to said secondary coil and said electrode array.

5. The prosthesis of claim 1 wherein said secondary coil is configured for mounting in said vitreous body with the axis of said secondary coil extending substantially coincident with the optic axis of the user's eye.

6. The prosthesis of claim l wherein said secondary coil is configured for mounting in said vitreous body with the axis of said secondary coil extending substantially perpendicular with the optic axis of the user's eye and proximate to temporal side of the sclera.

7. In combination with a user's eye characterized by a lens and a sclera wall enclosing a vitreous chamber containing a vitreous body, and including a retina supported adjacent to said vitreous body proximate to the intraocular side of said sclera wall, a visual prosthesis comprising:

a secondary coil for responding to input signal energy to produce an output signal, said coil being mounted in said vitreous chamber in thermal contact with said vitreous body;

an array of electrodes separate from said secondary coil, but electrically coupled to said secondary coil, and implanted proximate to said retina; and signal processing circuitry coupled to said secondary coil and responsive to said output signal for applying an image signal to said array of electrodes for electrically stimulating said retina to present an apparent image to said user.

8. The combination of claim 7 further including a hermetically sealed housing containing said signal processing circuitry; and wherein said housing is supported in said vitreous chamber in thermal contact with said vitreous body.

9. The combination of claim 8 wherein said housing defines first and second perpendicularly oriented dimensions and wherein the housing is oriented in said vitreous chamber with the lesser of said dimensions extending substantially perpendicular to the axis of said secondary coil.

10. The combination of claim 7 further including a housing containing said signal processing circuitry;

said housing being mounted proximate to the extracellular side of said sclera wall; and conductive wires electrically connecting said signal processing circuitry through said sclera wall to said secondary coil and said array of electrodes.

11. The combination of claim 7 wherein said secondary coil is mounted with its axis substantially coincident with the optic axis of said user's eye.

12. A visual prosthesis for at least partially restoring vision to a user suffering from a photoceptor degenerative condition, said prosthesis comprising:

an image acquiring portion for producing a real image signal representative of a real image; and a stimulating portion for electrically stimulating the user's retina to present an apparent image to the user;

said stimulating portion including:

an array of electrodes mounted in the user's eye proximate to said retina and electrically connected thereto; and a protective housing containing signal processing circuitry responsive to said real image signal for applying an apparent image signal to said electrode array for stimulating said retina to present said apparent image; and wherein said housing is mounted in the vitreous body of the user's eye in good thermal contact therewith.

13. The prosthesis of claim 12 wherein said image acquiring portion includes a primary coil; and said stimulating portion includes a secondary coil; and wherein said primary and secondary coils are mounted in close proximity tor coupling said real image signal from said image acquiring portion to said stimulating portion.

14. The prosthesis of claim 13 wherein said secondary coil is mounted in the vitreous body of the user's eye in good thermal contact therewith.

15. The prosthesis of claim 14 wherein said housing is oriented relative to said secondary coil to minimize the generation of eddy currents therein.

16. The prosthesis of claim 13 wherein said primary and secondary coils are supported substantially coincident with the optic axis of the user's eye.

17. A visual prosthesis for at least partially restoring vision to a user suffering from a photoceptor degenerative condition, said prosthesis comprising:

an image acquiring portion including an extracellular primary coil for producing a real image signal representative of a real image; and a stimulating portion for electrically stimulating the user's retina to present an apparent image to the user;

said stimulating portion including:

a secondary coil coupled to said primary coil for producing an output signal in response to said real image signal;

an array of electrodes mounted in the user's eye proximate to said retina and electrically connected thereto; and a protective housing containing signal processing circuitry responsive to said output signal for applying an apparent image signal to said electrode array for stimulating said retina to present said apparent image; and wherein said housing is mounted adjacent to the extracellular side of the user's sclera wall.

18. The prosthesis of claim 17 wherein said secondary coil is mounted in the vitreous body of the user's eye.

19. The prosthesis of claim 17 wherein said primary coil and said secondary coil are mounted substantially in alignment with the optic axis of the user's eye.

20. The prosthesis of claim 17 wherein said primary coil and said secondary coil are substantially aligned with one another along an axis displaced from the optic axis of the user's eye.

21. A method for implanting a visual prosthesis in the eye of a user including:

fixing a secondary coil in the vitreous chamber of the user's eye in thermal contact with the vitreous body in the chamber;

mounting a protective housing containing signal processing circuitry in close proximity to said secondary coil;

connecting an electrode array, separate from said secondary coil and said signal processing circuitry, to the user's retina; and electrically connecting said signal processing circuitry to said secondary coil and said electrode array.

* * * * *

UNITED STATES PATENT AND TRADEMARK OFFICE

CERTIFICATE OF CORRECTION

PATENT NO. : 7,103,416 B2
APPLICATION NO. : 09/761270
DATED : September 5, 2006
INVENTOR(S) : Jerry Ok, Robert J. Greenberg and Mark Humayun It is certified that error appears in the above-identified patent and that said Letters Patent is hereby corrected as shown below:

In the Claims:

Col. 6, claim 17, line 26, delete "extracellular" and replace with -- extraocular --.

Col. 6, claim 17, line 43, delete "extracellular" and replace with -- extraocular --.

Signed and Sealed this
Twenty-fifth Day of October, 2011

David J. Kappos
*Director of the United States Patent and Trademark Office*